US009921334B2

(12) United States Patent
Honarpour et al.

(10) Patent No.: US 9,921,334 B2
(45) Date of Patent: Mar. 20, 2018

(54) COMBINING MULTIPLE ENERGY X-RAY IMAGING AND WELL DATA TO OBTAIN HIGH-RESOLUTION ROCK, MECHANICAL, AND ELASTIC PROPERTY PROFILES

(71) Applicant: Ingrain, Inc., Houston, TX (US)

(72) Inventors: Mehdi Matt Honarpour, Houston, TX (US); Jack Dvorkin, Houston, TX (US)

(73) Assignee: Ingrain, Inc., Houston, TX (US)

( * ) Notice: Subject to any disclaimer, the term of this patent is extended or adjusted under 35 U.S.C. 154(b) by 186 days.

(21) Appl. No.: 14/910,736

(22) PCT Filed: Sep. 4, 2013

(86) PCT No.: PCT/US2013/057899
§ 371 (c)(1),
(2) Date: Feb. 8, 2016

(87) PCT Pub. No.: WO2015/034472
PCT Pub. Date: Mar. 12, 2015

(65) Prior Publication Data
US 2016/0195637 A1 Jul. 7, 2016

(51) Int. Cl.
*G01V 5/10* (2006.01)
*G01V 5/08* (2006.01)
(Continued)

(52) U.S. Cl.
CPC .............. *G01V 5/12* (2013.01); *G01N 23/046* (2013.01); *G01V 5/04* (2013.01); *G01V 11/00* (2013.01)

(58) Field of Classification Search
CPC . G01V 5/12; G01V 11/00; G01V 5/04; G01V 5/125; G01V 1/50; G06F 2217/16
(Continued)

(56) References Cited

U.S. PATENT DOCUMENTS 9,696,453 B2 * 7/2017 Freedman ................ G01V 5/08

OTHER PUBLICATIONS

International Search Report and Written Opinion issued in corresponding International Patent Application No. PCT/US2013/057899 dated Jun. 2, 2014 (12 pages).
(Continued)

*Primary Examiner* — Don Wong
(74) *Attorney, Agent, or Firm* — Chamberlain Hrdlicka

(57) ABSTRACT

A method is provided for evaluating a geological formation which integrates well data and high resolution computed tomography of rock samples thereof. Relationships are determined for a formation between a formation property, such as an elastic property, and at least one of photoelectric effect index (PEF), effective atomic number ($Z_{eff}$), and bulk density (RHOB), using well data, and tomographic imaging is used to determine at least one of the latter mentioned properties (PEF, $Z_{eff}$, RHOB) at higher resolution, which can be used in the relationship to determine a corresponding formation property. This affords an opportunity to develop formation property data for more challenging formations to evaluate, such as thinly laminated formations or others. Computerized systems, computer program products on non-transitory computer usable storage media, and programs for performing the methods are also provided.

26 Claims, 10 Drawing Sheets

(51) Int. Cl.
  *G01V 5/12*  (2006.01)
  *G01V 5/04*  (2006.01)
  *G01V 11/00*  (2006.01)
  *G01N 23/04*  (2018.01)

(58) Field of Classification Search
  USPC .......................................... 378/5; 250/269.3
  See application file for complete search history.

(56) References Cited

OTHER PUBLICATIONS

Derzhi et al., "Comparison of traditional and digital rock physics techniques to determine the elastic core parameters in Cretaceous formations, Abu Dhabi," SPE-138586-PP, SPE International, Abu Dhabi International Petroleum Exhibition & Conference, Abu Dhabi, UAE, Nov. 1, 2010, pp. 1-8.

Tovar et al., "Looking Into La Luna," Oilfield Technology Magazine, Jul. 2013, (2 pages).

Wallis et al., "Digital Rock Physics," Oilfield Technology, Mar. 2012, (3 pages).

Walls et al., "Shale Reservoir Evaluation Improved by Dual Energy X-Ray CT Imaging," JPT, Nov. 2012, pp. 28-32.

Zhan et al., "Study Geophysical Response of Middle East Carbonate Reservoir using Computational Rock Physics Approach," SEG Las Vegas 2012 Annual Meeting, 2012, pp. 1-5.

\* cited by examiner

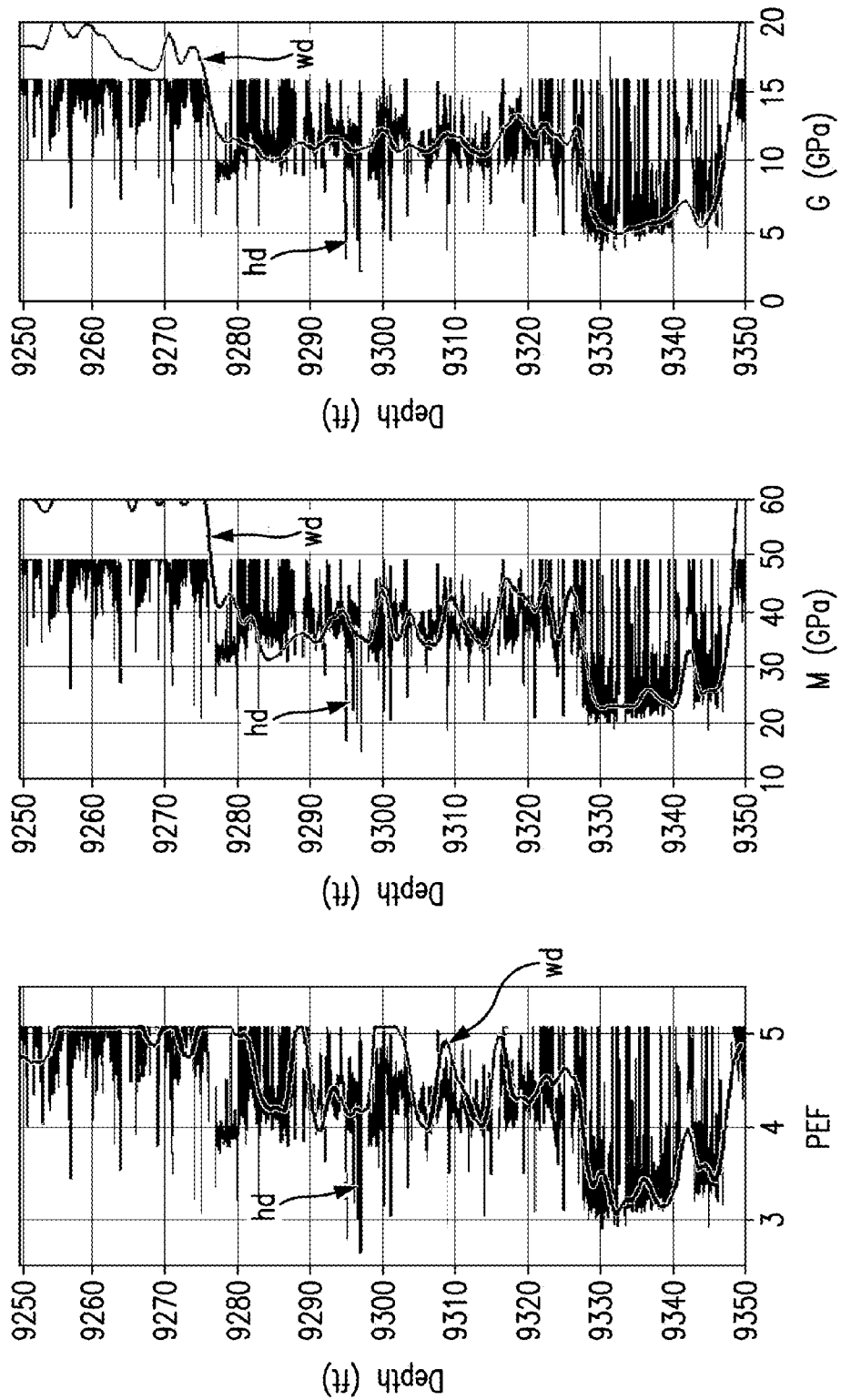

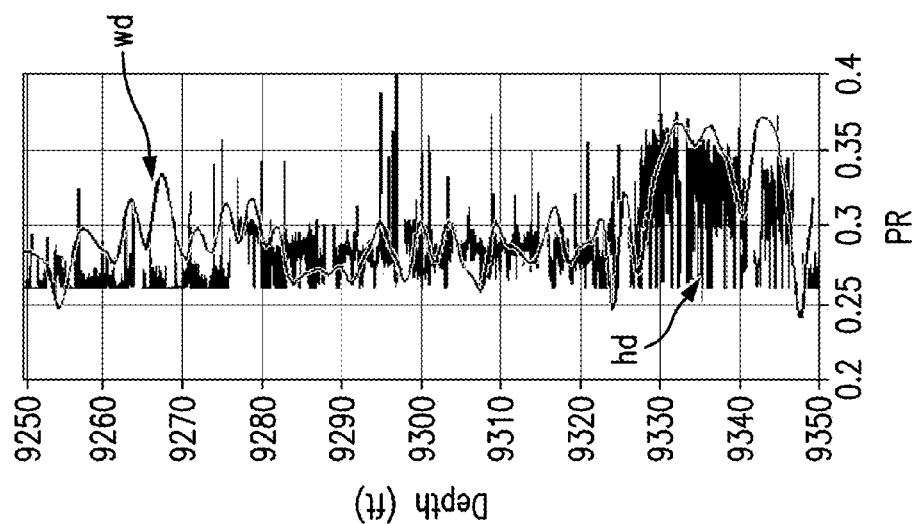
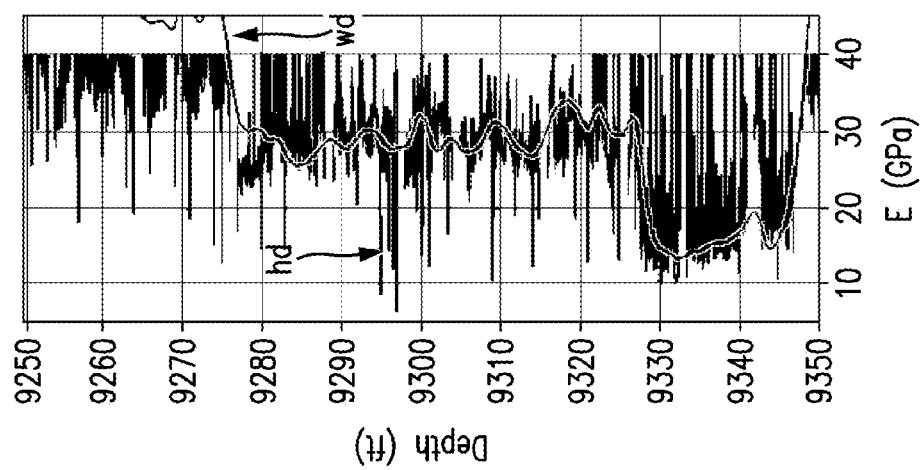
FIG. 3E
FIG. 3D

COMBINING MULTIPLE ENERGY X-RAY IMAGING AND WELL DATA TO OBTAIN HIGH-RESOLUTION ROCK, MECHANICAL, AND ELASTIC PROPERTY PROFILES

This application is a National Stage Application of PCT/US2013/057899, filed Sep. 4, 2013.

BACKGROUND OF THE INVENTION

The invention relates generally to the field of geological formation evaluation and, more particularly, to a method for evaluating a geological formation which integrates well data and high resolution computed tomography of rock samples thereof. A system for performing the method also is provided.

Well log measurements can provide a number of rock properties needed to plan well completion and lateral placement. These properties include mineralogy, bulk density, porosity, electrical resistivity and elastic-wave velocities. Elastic-wave velocities and bulk density can be used to compute the elastic moduli needed to estimate the mechanical properties and strength of the formation. These mechanical properties are important for planning deviated and lateral wells and for fracture treatment. However, conventional well data resolution typically is only about 1.5 to 1.0 feet (about 46 cm to about 30 cm). This well data resolution typically is not high enough for evaluating some formations, such as thinly laminated formations which have thicknesses below the indicated level of resolution feasible with conventional well data.

Shale is an unconventional source of oil and/or gas. Shale rocks have not been studied extensively due to the fact that they traditionally were thought of as the source rock and not a potential reservoir because of their low porosity and permeability values. However, there are new methods to extract the oil and gas within these rocks, and therefore, there is great interest in analysis methods to characterize these rocks to better understand the mechanics of production from shales. Well data resolution alone typically is not high enough for evaluating thinly laminated formations of shale. The scale of lamination of shale can be measured in the cm or mm range significantly less than 1 foot (30 cm). Traditionally, there were only limited ways to analyze shale samples, and this began with scanning electron microscopes (SEM). The SEM image provides a two-dimensional (2D) picture or image of the sample that typically has a resolution of approximately 15-100 nanometers. Using only two-dimensional images, however, one is only able to estimate porosity and organic content. 3D CT imaging and/or FIB-SEM (focused ion beam combined with SEM) imaging have been proposed for evaluating some properties of shale, such as identification of the components, including the mineral phases, organic-filled pores, and free-gas inclusions; and computations of TOC (Total Organic Content), porosity, pore connectivity, and permeability in the three axis. Sisk et al, SPE 134582, "3D Visualization and Classification of Pore Structure and Pore Filling in Gas Shales", 2010; Curtis et al, SPE 137693, "Structural Characterization of Gas Shales on the Micro- and nano-Scales", 2010; Milner et al, SPE 138975, "Imaging Texture and Porosity in Mudstones and Shales: Comparison of Secondary and Ion-Milled Backscatter SEM methods", 2010. However, this digital rock physics technology, e.g., 3D CT imaging and/or FIB-SEM technology, does not directly provide the elastic properties needed for computing the elastic moduli and other mechanical properties of the formation.

There remains a need for methods and systems to provide evaluations of geological formations that can combine well data with higher resolution digital rock physics in determining formation properties such as elastic properties or other mechanical properties thereof.

SUMMARY OF THE INVENTION

A feature of the present invention is a method for evaluating a geological formation that integrates well data and higher-resolution computed tomography, wherein high-resolution rock property values and profiles can be obtained.

An additional feature of the present invention is a method for evaluating a geological formation that establishes a formulaic relationship of density, photoelectric effect index or effective atomic number to a different formation property based on well data, laboratory data, or theoretical modeling that can be applied to values of density, photoelectric effect index, or effective atomic number determined for formation samples using computed tomography at a much higher resolution scale to obtain high-resolution elastic properties or other properties of the formation.

Another feature of the present invention is system for performing the indicated methods.

To achieve these and other advantages and in accordance with the purposes of the present invention, as embodied and broadly described herein, the present invention relates, in part, to a method for evaluating a geological formation, which comprises (a) determining a first parameter comprising photoelectric effect index, effective atomic number, or bulk density, and a target parameter comprising a formation property that is different from the first parameter, for a rock sample at a depth interval in a formation using formation data (e.g., well data, laboratory data, non-tomographic theoretical modeling data, or any combinations thereof); (b) repeating (a) for at least one additional depth interval in the formation; (c) curve-fitting the first parameter and the target parameter determined for the depth intervals of (a)-(b) to generate at least one of a mathematical function equation or cross-plot thereof relating the first and target parameters; (d) generating a tomographic image of a rock sample obtained from a depth interval in the formation for generating a digital image of the rock sample; (e) determining photoelectric effect index, effective atomic number, or bulk density in correspondence to the first parameter used in the curve-fitting in (c) for the rock sample of (d), using the digital image generated for the rock sample in (d); and (f) computing a high resolution target parameter for the rock sample of (d) comprising applying the mathematical function equation or cross-plot of (c) to the photoelectric effect index, effective atomic number, or bulk density determined in (e).

The present invention also relates to a method for evaluating a geological formation, comprising (a) determining a first parameter comprising photoelectric effect index, effective atomic number, or bulk density, and a target parameter comprising an elastic modulus property, for a rock sample at a depth interval in a formation using well logging data; (b) repeating (a) for at least one additional depth interval in the formation; (c) curve-fitting the first parameter and the target parameter determined for the depth intervals of (a)-(b) to generate at least one of a mathematical function equation or cross-plot thereof relating the first and target parameters; (d) performing an X-ray CT scan of a rock sample obtained from a depth interval in the formation for generating a digital image of the rock sample; (e) determining photoelectric effect index, effective atomic number, or bulk density in correspondence to the first parameter used in the curve-fitting in (c) for the rock sample of (d), using CT values obtained for voxels in the digital image generated for the rock sample from the X-ray CT scan in (d); and (f) computing a high resolution target parameter for the rock sample of (d) comprising applying the mathematical function equation or cross-plot of (c) to the photoelectric effect index, effective atomic number, or bulk density determined in (e).

The present invention also relates to a method for evaluating a geological formation, which comprises (a) determining multiple parameters among photoelectric effect index, effective atomic number, and bulk density, and a target parameter comprising a formation property that is different from the multiple parameters, for a rock sample at a depth interval in a formation using formation data (e.g., well data, laboratory data, non-tomographic theoretical modeling data, or any combinations thereof); (b) repeating (a) for at least one additional depth interval in the formation; (c) curve-fitting the multiple parameters and the target parameter determined for the depth intervals of (a)-(b) to generate at least one of a multivariable mathematical function equation or 3D plot thereof relating the target parameter as a function of the multiple parameters; (d) generating a tomographic image of a rock sample obtained from a depth interval in the formation for generating a digital image of the rock sample; (e) determining more than one of photoelectric effect index, effective atomic number, or bulk density in correspondence to the multiple parameters used in the curve-fitting in (c) for the rock sample of (d), using the digital image generated for the rock sample in (d); and (f) computing a high resolution target parameter for the rock sample of (d) comprising applying the multivariable mathematical function equation or 3D plot of (c) to the more than one of photoelectric effect index, effective atomic number, or bulk density determined in (e).

Computerized systems, computer program products on non-transitory computer usable storage media, and programs for performing the methods are also provided.

Additional features and advantages of the present invention will be set forth in part in the description that follows, and in part will be apparent from the description, or can be learned by practice of the invention. The features and other advantages of the present invention will be realized and attained by means of the elements and combinations particularly pointed out in the description and appended claims.

It is to be understood that both the foregoing general description and following detailed description are exemplary and explanatory only and are intended to provide a further explanation of the present invention, as claimed.

A BRIEF DESCRIPTION OF THE DRAWINGS

The accompanying drawings, which are incorporated in and constitute a part of this application, illustrate features of the present invention and, together with the description, serve to explain the principles of the present invention. The same items in different figures are designated with the identical reference numerals and related items are often designated with the same reference numerals with a letter suffix appended.

FIGS. 1A-1G show formation property profiles as a function of well depth in a well drilled through a light oil-bearing interval with the well data obtained by well logging according to an example of the present invention. In these figures, FIG. 1A shows gamma ray (GR, API units) data with respect to well depth (feet). FIG. 1B shows $Log_{10}$ electrical resistivity ($\Omega \cdot m$) data with respect to well depth (ft). FIG. 1C shows photoelectric effect index (PEF, unitless) data with respect to well depth (ft). FIG. 1D shows bulk density (RHOB, g/cc) data with respect to well depth (ft). In the porosity track in FIG. 1E, the "PhiT" curve is the total porosity; the "PhiRHO" curve is the density-derived porosity computed by assuming the matrix is pure calcite; and the "NPHI" curve is the total porosity. FIG. 1E shows porosity (fraction) data with respect to well depth (ft). FIG. 1F shows data for elastic wave velocities Vs (shear or S-wave velocity, km/s) and Vp (compressional or P-wave velocity, km/s) with respect to well depth (ft). FIG. 1G shows Poisson's ratio (PR) data as a function of depth (ft).

FIGS. 3A-3E are depth plots of elastic moduli obtained by applying equations that were generated based on data obtained for elastic moduli data and PEF data from wellbore logging to high-resolution photoelectric effect index (PEF) data obtained from multi-energy X-ray CT scanning of samples from the same formation. In these figures, FIG. 3A is a depth plot of lower resolution photoelectric index (PEF) data (wd) obtained by wellbore logging and high-resolution photoelectric effect index (PEF) data (hd) provided from multi-energy X-ray CT scanning measurements of samples from the same formation. FIG. 3B is a depth plot of compressional modulus (M, in GPa) obtained by applying the equation of FIG. 2B to high-resolution photoelectric effect index (PEF) data provided from multi-energy X-ray CT scanning measurements of samples from the same formation. FIG. 3C is a depth plot of shear modulus (G, in GPa) obtained by applying the equation of FIG. 2C to high-resolution photoelectric effect index (PEF) data provided from multi-energy X-ray CT scanning measurements of samples from the same formation. FIG. 3D is a depth plot of Young's modulus (E, in GPa) obtained by applying an equation developed similarly as equations in FIGS. 2B and 2C as adapted for Young's modulus and PEF to high-resolution photoelectric effect index (PEF) data provided from multi-energy X-ray CT scanning measurements of samples from the same formation. FIG. 3E is a depth plot of Poisson's ratio (PR) obtained by applying an equation developed similarly as equations in FIGS. 2B and 2C as adapted for Poisson's ratio and PEF to high-resolution photoelectric effect index (PEF) data provided from multi-energy X-ray CT scanning measurements of samples from the same formation. In FIGS. 3A-3E, the lighter curves "hd" indicate the high-resolution multi-energy X-ray CT scanning-derived values and the darker black curves "wd" indicate the wellbore data.

Figure 4:
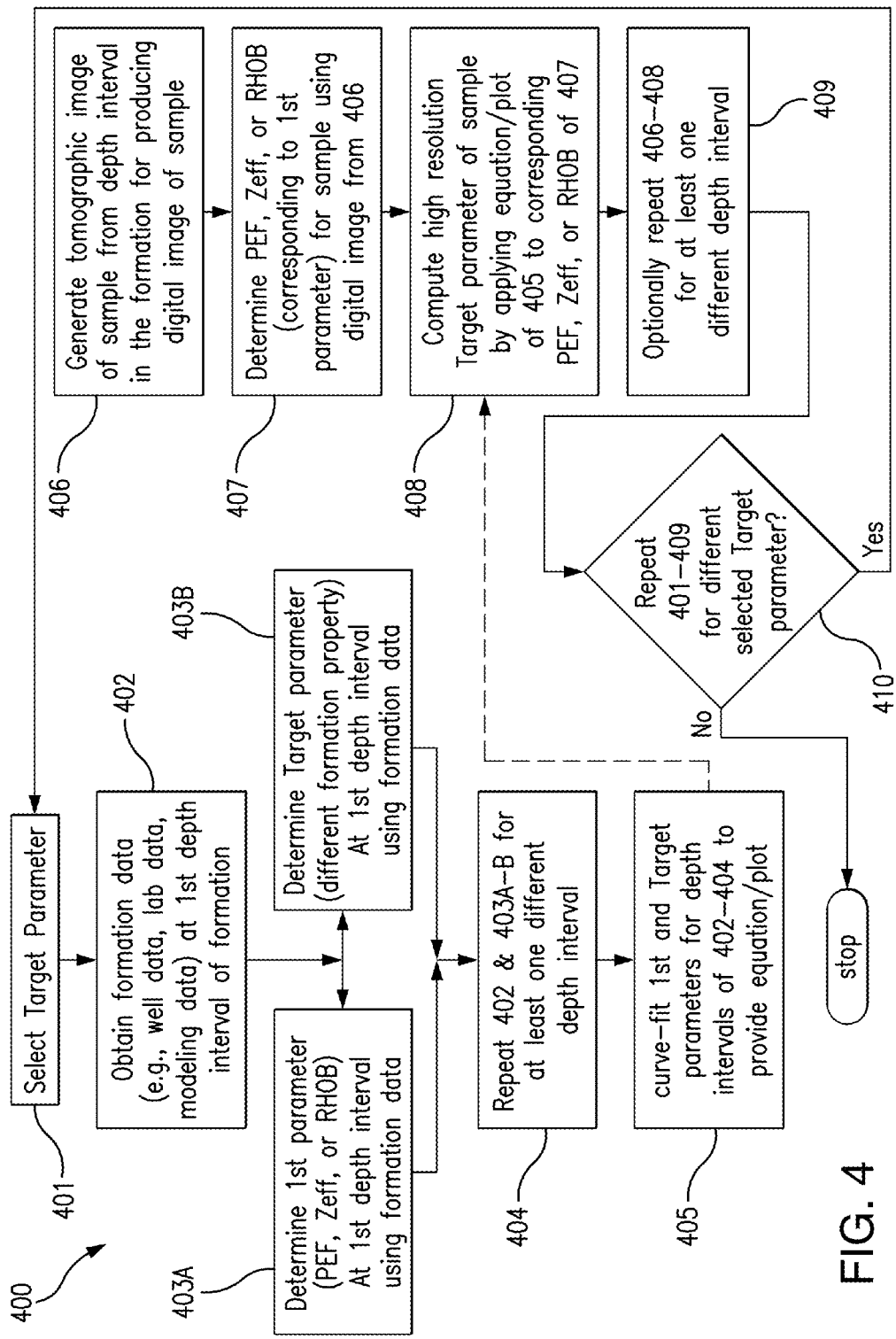

FIG. 4 is a flow diagram illustrating a work flow in accordance with an example of the present application.

Figure 5:
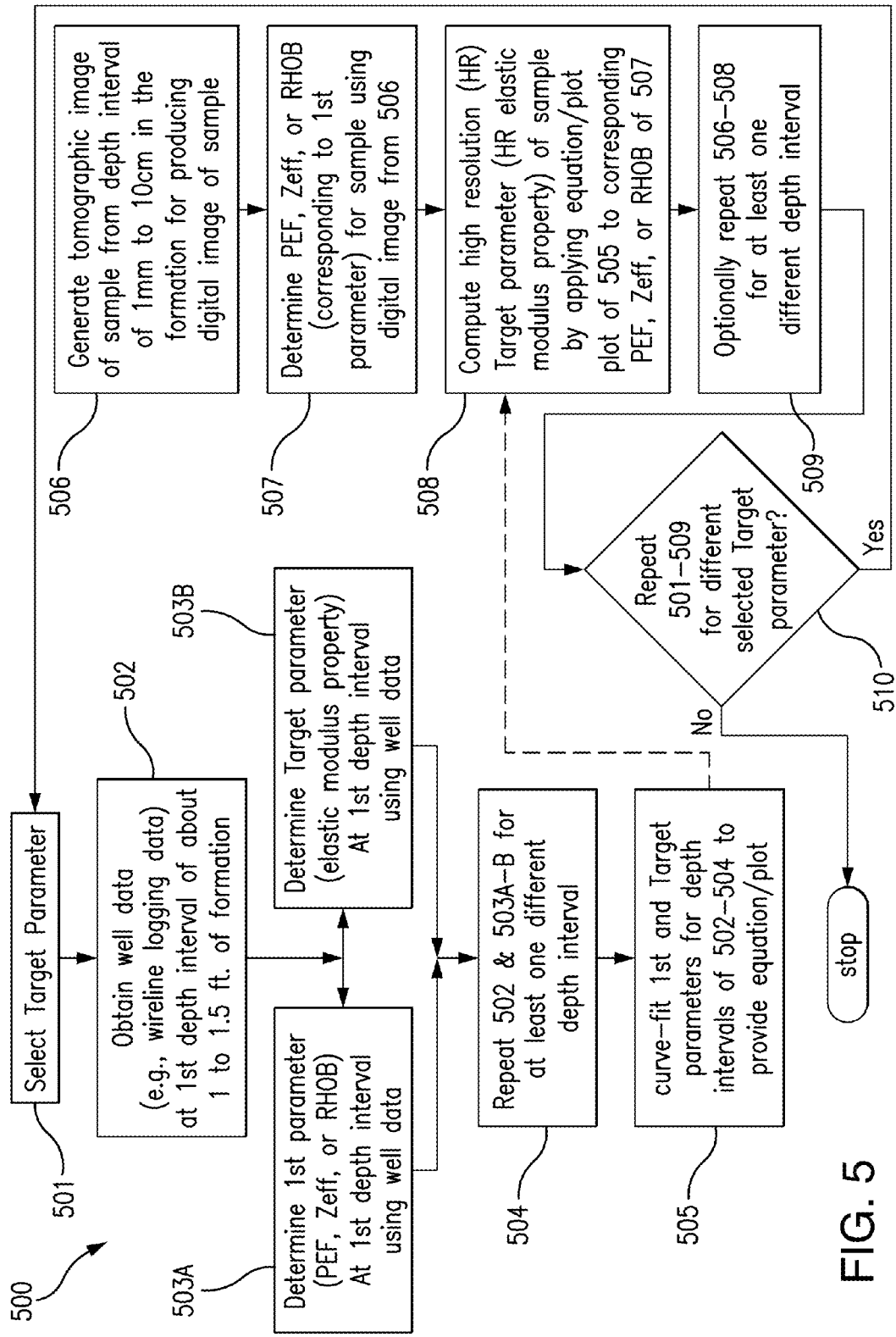

FIG. 5 is a flow diagram illustrating another work flow in accordance with an example of the present application.

Figure 6:
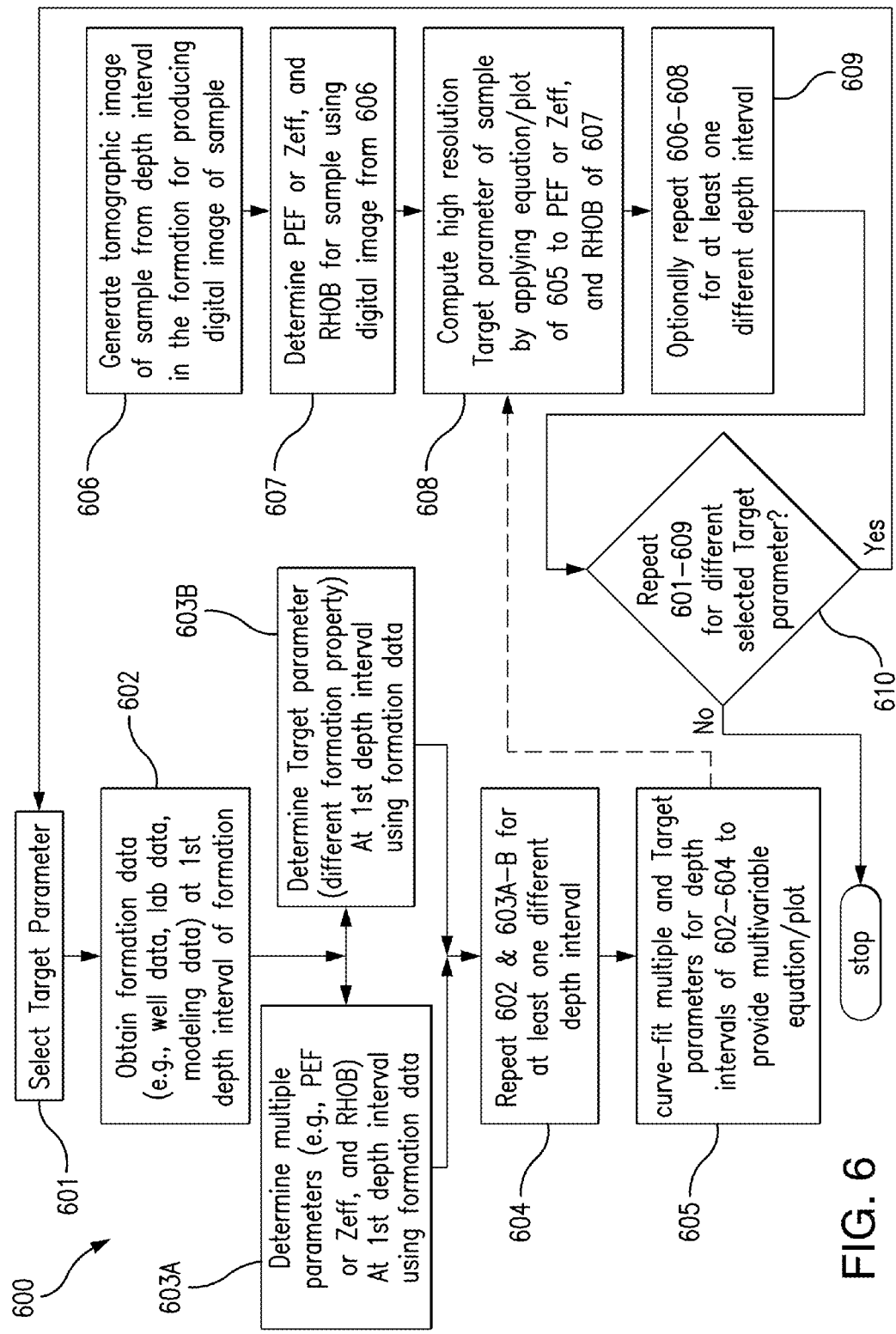

FIG. 6 is a flow diagram illustrating another work flow in accordance with an example of the present application.

Figure 7:
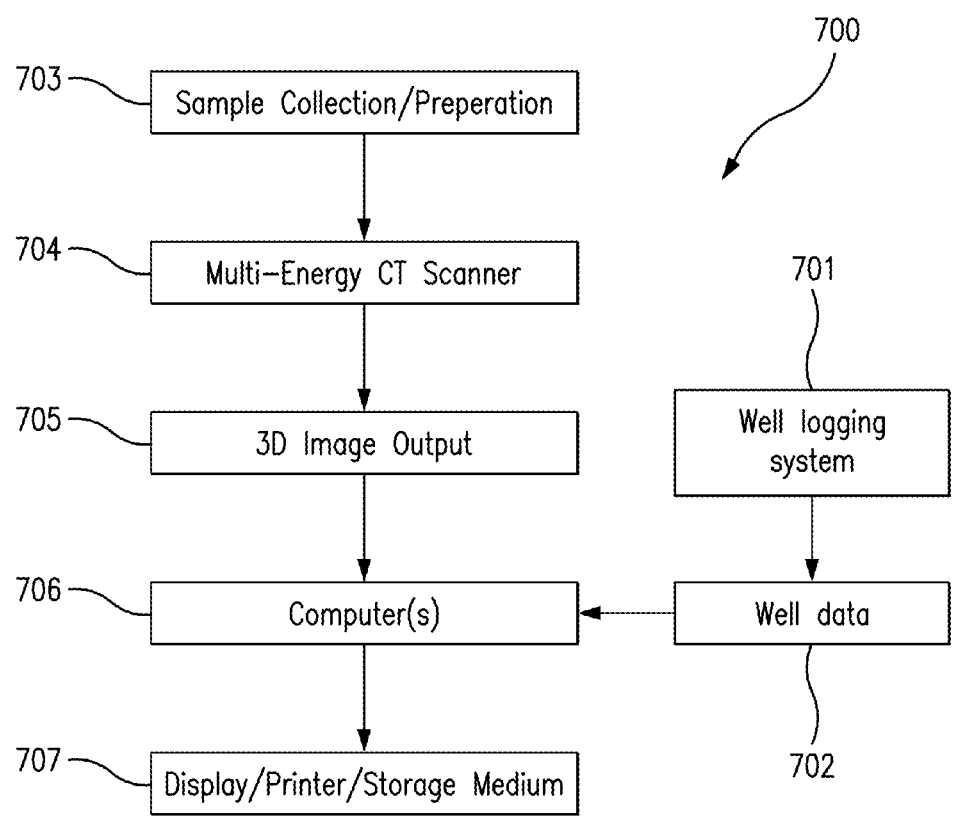

FIG. 7 is a system according to an example of the present application.

DETAILED DESCRIPTION

The present invention relates in part to methods and systems for evaluating a geological formation which integrates well data (or other non-tomographic data) and computed tomography of rock samples thereof to provide high resolution estimations of formation properties. Conventional well data resolution, such as well logging data, is not high enough in thinly laminated formations, such as shale, where the scale of lamination can be measured in cm or mm. The present invention can fit well data or other non-tomographic based formation data for different parameters into one or more formulaic relationships. These formulaic relationships can be applied to high resolution data obtained by computed tomography on one or more of the parameters in common to the well data or other non-tomographic based data. This combination can be used to estimate a formation property or properties that computed tomography itself usually cannot directly provide, such as elastic properties, or other properties. Multi-energy computed tomography of core materials can provide the variables of bulk density, and photoelectric effect (PEF) (or effective atomic number). However, the technology of multi-energy computed tomography of core materials does not directly provide the elastic properties required for computing the elastic moduli and mechanical properties of the formation. Using a method of the present invention, elastic properties that usually cannot be provided by computed tomography of core material, can be estimated by cross-referencing a parameter value that can be provided at high resolution by computed tomography with a formulaic relationship developed from the well data or other non-tomographic data that includes that same parameter. It has been surprisingly found that the formulaic relationships developed from relatively lower resolution well data or other non-tomographic data can be used with high resolution data obtained by CT scanning to reliably estimate elastic properties or other formation properties at high resolution for rock samples of the formation. This can be highly useful in evaluating elastic properties or other formation properties of thinly laminated formations, such as shale formations at the 1 mm to 10 cm thickness scale or others, which may be amenable to high resolution evaluation by tomographic scanning for some properties other than elastic properties, but not with conventional well logging or laboratory data.

In many geological formations, robust relations can be found between the bulk density and the elastic moduli, or photoelectric effect index (PEF) (or effective atomic number) and the elastic properties, or other formation properties. Such relations can be empirical and site-specific (local) or more general and theory based. Formulaic relationships can be determined for a geological formation between a formation property, such as an elastic property, and at least one of photoelectric effect index (PEF), effective atomic number ($Z_{eff}$), and bulk density (RHOB), using well data or other non-tomographic data. The formulaic relationship can be obtained from curve-fitting applied to the well data or other non-tomographic based data. Curve fitting is a process of constructing a curve, or mathematical function (e.g., a polynomial function), that has the best fit to a series of data points, possibly subject to constraints. Curve fitting can involve either interpolation, where an exact fit to the data is required, or smoothing, in which a "smooth" function is constructed that approximately fits the data. The curve fitting can be polynomial curve fitting, or other types. The formulaic relationship that is obtained by curve fitting can be expressed and used mathematically, graphically (plotted), or both. An ordinary least-squares (algebraic fit) line obtained, for example, can be plotted on a graph for the well data or other non-tomographic data for at least two different kinds of formation data parameters. Tomographic imaging can be used to determine at least one of the properties PEF, $Z_{eff}$, and RHOB at higher resolution, which can have the formulaic relationship or a plot thereof applied thereto to determine a formation property associated with the tomographic-obtained property value. The formation property that is estimated by applying the formulaic relationship generated from well data and the like to a tomographic-obtained value of PEF, $Z_{eff}$, or RHOB can be an interpolated or extrapolated value. As indicated, this method of the present invention is capable of developing high resolution formation property data for more challenging formations, such as thinly-laminated shale formations or others. Computerized systems, computer program products on non-transitory computer usable storage media, and programs for performing the methods are also provided.

The well data can be field-based, such as well logging data (e.g., wireline logging data or logging-while-drilling (LWD) data), or can include such well data in combination with other forms of non-tomographic based data on a formation. "Well logging" also can be referred to as "borehole logging" or "downhole logging." Well logging instruments having photon sources and photon detectors can be used to evaluate earth formation lithology by making use of the photoelectric effect to derive an effective atomic number for an earth formation. Typical lithology well logging techniques and wireline tools that can be used to obtain the well data include those commercially available, and those such as in U.S. Pat. No. 4,691,102, which is incorporated by reference in its entirety. The formation data can be laboratory data, or can include laboratory in combination with other forms of non-tomographic formation data. The formation data can be non-tomographic based theoretical reservoir modeling data, or can include non-tomographic based theoretical modeling data in combination with other forms of non-tomographic formation data, such as indicated herein. Well log measurements, for example, can provide a number of rock properties needed to plan well completion and lateral placement. These properties can include mineralogy, bulk density, porosity, electrical resistivity, and elastic-wave velocities. Elastic-wave velocities and bulk density can be used to compute the elastic moduli needed to estimate the mechanical properties and strength of the formation. The elastic constants can include shear modulus (G), compressional modulus (M), Poisson's Ratio (PR), Young's Modulus (E), and the bulk modulus of compressibility (K). These mechanical properties can be important for planning deviated and lateral wells and for fracture treatment. However, as indicated, the well data resolution usually is only about 1.5 to 1.0 ft. As indicated, this resolution is not high enough to capture data on thinly laminated formations, such as shale, where the scale of lamination can be measured in cm or mm (e.g., 1 mm to 10 cm, or other values less than 1 foot). Static elastic constants can be derived for rock samples in a laboratory, such as from tri-axial stress strain measurements (non-destructive) or the chevron notch test (destructive).

However, laboratory testing can be time-consuming and the resolution is not high enough for evaluating thinly laminated formations.

According to an example of the present invention, a method is provided for evaluating a geological formation that can establish a formulaic relationship based on well data for density, photoelectric effect index, or effective atomic number to at least one elastic property, such as at least one of compressional modulus (M), shear modulus (G), or another elastic property. The formulaic relationship established using the well data then can be applied to values of density, photoelectric effect index, or effective atomic number that are determined for formation samples using computed tomography at a much higher resolution than possible with the well data, to obtain high-resolution (e.g., mm scale) elastic properties, mechanical properties or other properties of the formation, such as at the depth interval or intervals at which the samples were obtained. An elastic property or other formation property estimated using the formulaic relationship in such manner can be further used for computing elastic moduli, mechanical properties, or other properties and characteristics of the formation. The same principle can be used for any other formation property that is available from well data or other non-tomographic data on a formation.

Referring to FIGS. 1A-1G, these figures show formation property profiles in a Well A, drilled through a light-oil bearing interval. From left to right in these figures, profiles for Gamma Ray (GR); Decimal Logarithm of Resistivity; photoelectric effect index (PEF); bulk density (RHOB); porosity; P-wave velocity ($V_p$) and S-wave velocity ($V_s$); and Poisson's ratio (PR) are shown. Elastic moduli, such as compressional modulus (M), shear modulus (G), Poisson's ratio (PR), Young's modulus (E), and bulk modulus (K), can be calculated with the bulk density (RHOB) and wave velocities obtained from the wellbore data using known equations. For example, $M=RHOB(V_p)^2$; $G=RHOB(V_s)^2$; $PR=\frac{1}{2}\cdot[(M/G-2)/(M/G-1)]$; $E=2G(1+PR)$; and $K=M-(4/3)G$.

Figure 1D:
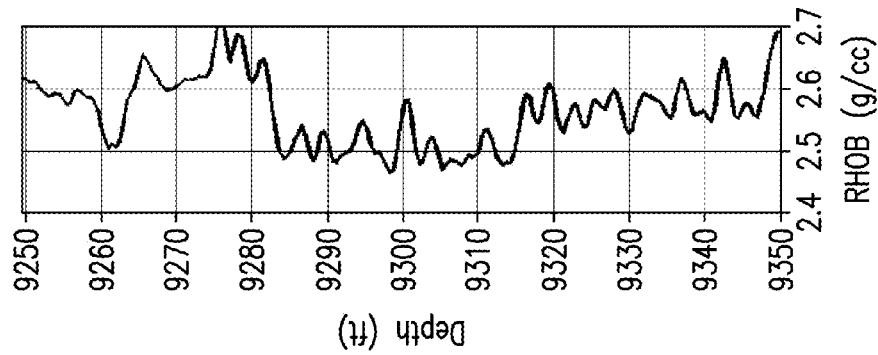
Figure 1C:
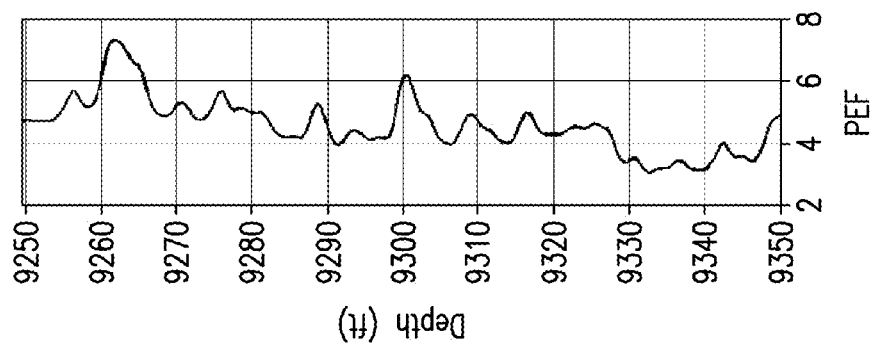
Figure 1B:
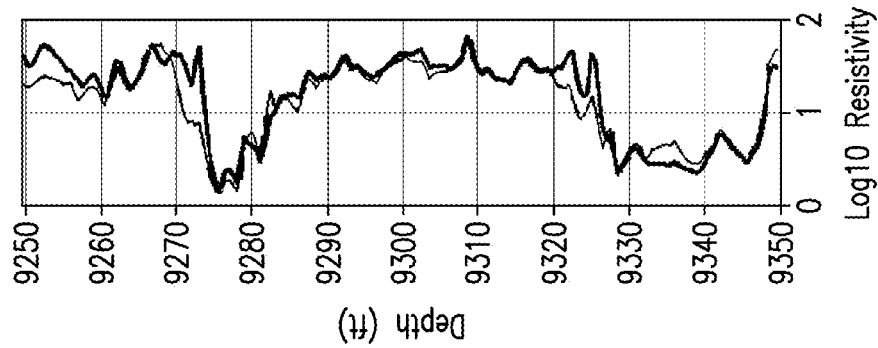
Figure 1A:
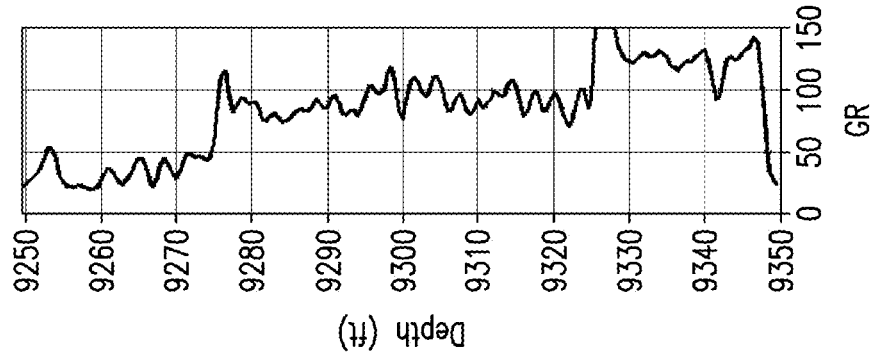
Figure 1G:
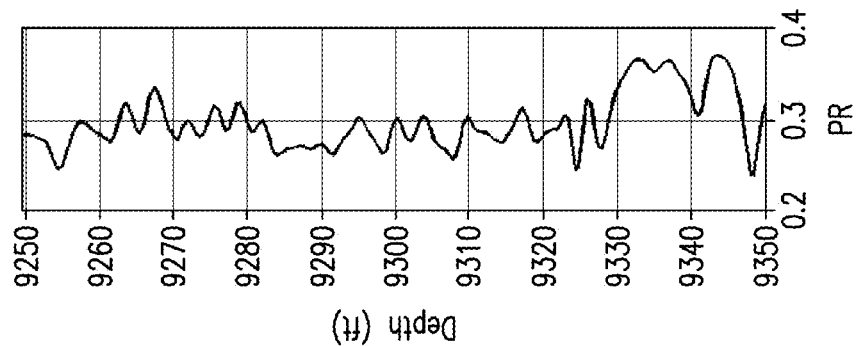
Figure 1F:
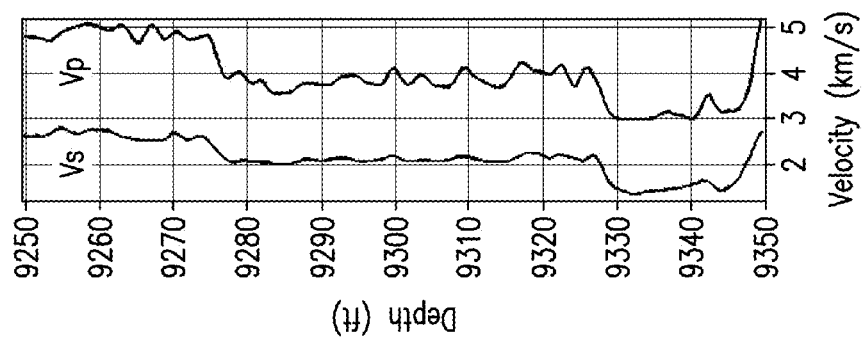
Figure 1E:
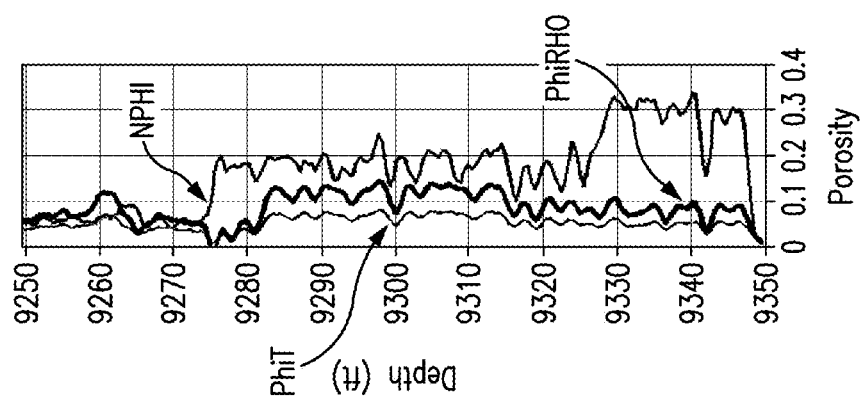
Figure 2A:
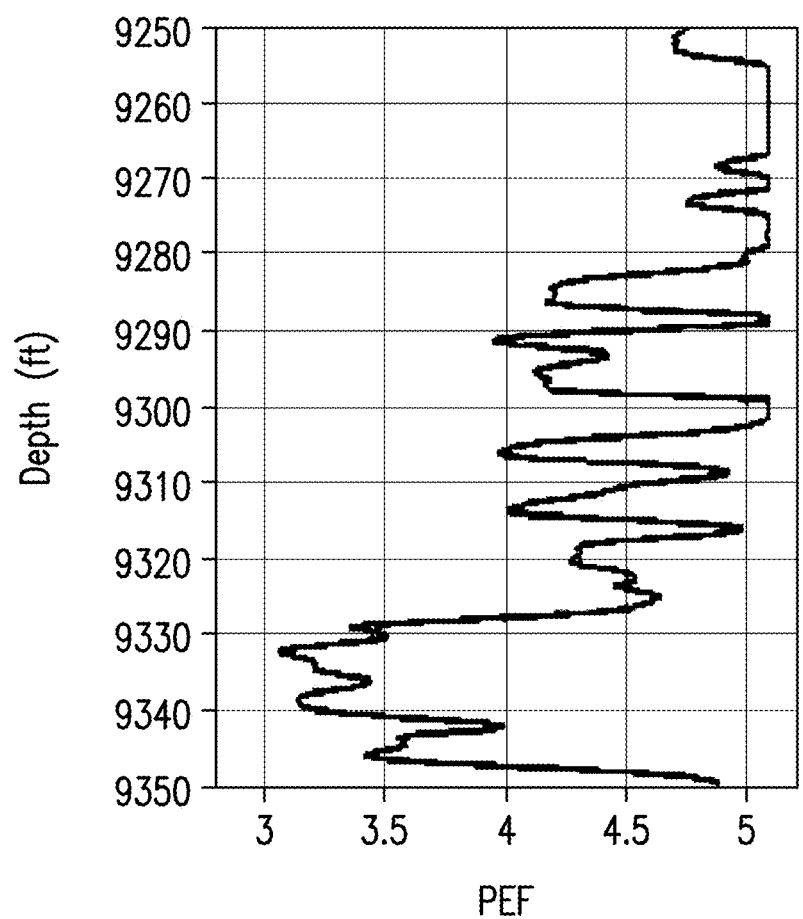
FIG. 2A is a plot of between photoelectric effective index (PEF) and depth (ft) in the well based on the data shown in FIG. 1C according to an example of the present application. The straight vertical line portions of the curve represent the PEF at a value of 5.084 thereof, and the remainder of the curve is the measured PEF.
Figure 2B:
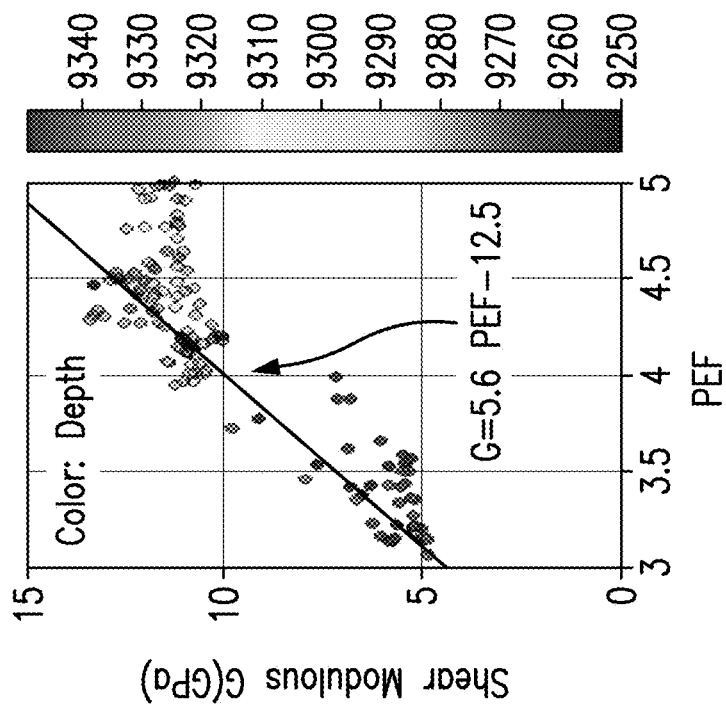
FIG. 2B is a cross-plot between photoelectric effective index (PEF) and compressional modulus (M)(GPa) measured and computed in the well based on the data shown in FIGS. 1C-1G according to an example of the present application. The black line is a manual linear curve fit of the data with the line equation listed in the plot.
Figure 2C:
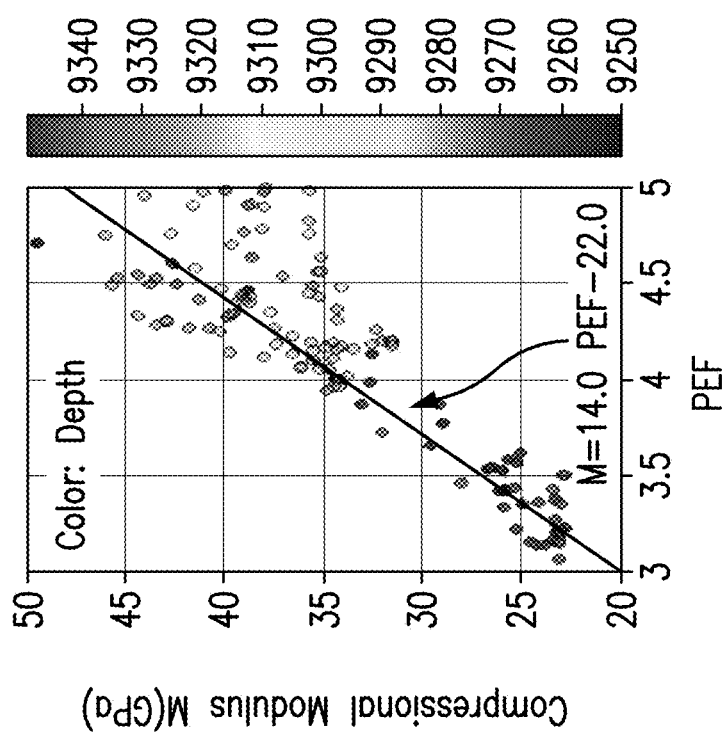
FIG. 2C is a cross-plot between photoelectric effective index (PEF) and shear modulus (G)(GPa) measured and computed in the well based on the data shown in FIGS. 1C-1G according to an example of the present application. The black line is a manual linear curve fit of the data with the line equation listed in the plot.

FIG. 2A is a plot of PEF versus depth for the well. FIGS. 2B and 2C shows cross-plots between photoelectric effect index (PEF) and the compressional and shear moduli, respectively, measured and computed in the well. The black line in FIGS. 2B and 2C is a manual linear fit with the equation listed in the respective plot. The relationship can be any other type of trends, depending on the data. The manually drawn linear relations between PEF and the aforementioned elastic moduli are defined by the equations (1):

$$M=14.0\text{PEF}-22.0; \quad G=5.6\text{PEF}-12.5, \quad (1)$$

where the moduli are expressed in units of GPa.

Further, although FIGS. 2B and 2C illustrate the method using the elastic constants M and G as a function of photoelectric effect index (PEF values), PEF values can be converted to effective atomic number (Zeff values), or vice versa (if Zeff is known), and either PEF or Zeff values can be used in methods of the present application. PEF and effective atomic number (Zeff) are related by the equation (2): $\text{PEF}=(Z_{Eff}/10)^{3.6}$. This equation can be used or manipulated to calculate PEF or Zeff, if the other parameter in the equation is known. Accordingly, cross-plots of M and Zeff, or G and Zeff, can be readily generated and used in methods of the present application in a similar manner as shown herein for the crossplots of M and PEF in FIG. 2B, and G and PEF in FIG. 2C. Furthermore, the crossplots can be based on the same or different elastic constant or constants as a function of bulk density (RHOB) obtained from the well data or other non-tomographic formation data. The data in these cross-plots can be curve fit to capture the trend in the data by assigning a single mathematical function across the entire range. Commercial curve-fitting and regression software can be adapted to curve fit the well data or other non-tomographic formation data in this respect. For example, MATLAB® software (MathWorks, Natick, Mass., U.S.A.) can be used for the curve fitting of the well data, laboratory data, or both.

FIGS. 3A-3G show the high-resolution profiles of the elastic moduli obtained by applying equations based on data obtained for elastic moduli data and PEF data from wellbore logging data to high-resolution PEF data provided by multi-energy CT scans of samples of the Well A. For example, FIGS. 3B and 3C show the elastic moduli obtained by applying Equations (1) for M and G to high-resolution PEF data provided by multi-energy CT scans of samples of the Well A. These figures are presented as depth plots of (left to right) PEF, compressional modulus, shear modulus, Young's modulus and Poisson's ratio. The lighter curves indicate the high-resolution multi-energy CT scan-derived values and the darker black curves indicate the wellbore data. These results show that the method of the present application can provide higher resolution for thinly laminated formations, such as shale, where the scale of lamination can be measured in cm or mm.

Referring to FIG. 4, a process flow 400 of a method of the present invention is illustrated which includes steps 401-410. As illustrated in this figure, a target parameter is selected for evaluation (401), and formation data (e.g., well data, lab data, modeling data) is obtained at a first depth interval for (402). The obtained formation data is used in determining a first parameter comprising at least one of photoelectric effect index, effective atomic number, and bulk density (403A), and a target parameter, as a second parameter, comprising a formation property that is different from the first parameter (403B), for a rock sample at the depth interval. This determining can refer to determining numerical values for the indicated first and target parameters. Steps 402 and 403A-B can be repeated for at least one additional depth interval in the formation (404). The first parameter and the target parameter determined for the depth intervals in steps 402, 403A-B, and 404, is curve fitted to generate at least one of a mathematical function equation or cross-plot thereof relating the first and target parameters (405). For example, as illustrated in FIG. 2B, a mathematical function equation and cross-plot are generated which relate compressional modulus (M), as the selected target parameter, as a function of PEF. Referring again to FIG. 4, a tomographic image is made of a rock sample obtained from a depth interval in the formation for generating a digital image of the rock sample (406). In step 407, at least one of photoelectric effect index, effective atomic number, or bulk density is determined in correspondence to the first parameter used in the curve-fitting in step 405 for the rock sample scanned in step 406, using the digital image generated for the rock sample in step 406. A high resolution target parameter of the rock sample scanned in step 406 is computed in step 408 comprising applying the mathematical function equation or cross-plot of step 405 to the corresponding parameter type of the photoelectric effect index, effective atomic number, and bulk density determined in step 407. In step 408, the high resolution target parameter can be calculated at higher resolution than for the original target parameter of step 403B where the same depth interval is compared. As can be appreciated, a depth interval selected in step 406 does not need to be identical to a depth interval selected in step 403B since the equation or plot generated in step 405 can permit interpolation, extrapolation, or both. Steps 406, 407 and 408 can be repeated for samples obtained from at least one different depth interval of the formation, or for multiple samples obtained from the same depth interval, or both (409). As can be appreciated, the use of PEF, Zeff, or RHOB, as the first parameter used in the process flow 400 shown in FIG. 4 is for sake of illustration only. The target parameter selected for evaluation in this process flow is not necessarily limited, and can be an elastic modulus property or related property (e.g., M, G, E, PR, Vp, Vs, etc.), or other property that can be expressed as a function of PEF, Zeff, or RHOB values. The method indicated as process 400 in FIG. 4 can be used to compute a higher resolution value for a selected target property at one or more depth intervals of a wellbore than can be obtained from wellbore logging data alone. As indicated by step 410, the process of steps 401-409 can be repeated for a different selected target parameter from that already evaluated using the process flow. The entire process flow optionally can be repeated any number of desired or needed times for additional different selected target properties, as evaluated one at a time by the process. The formation data that was obtained in step 402 and the first parameter values determined in step 403 of a previous evaluation of a target parameter using steps 402-409 may be applicable at least in part for use in a successive evaluation of a different target parameter. A method of the present invention can be based on a subset of these steps, and may include additional steps.

Referring to FIG. 5, a process flow 500 of a method of the present invention is illustrated which includes steps 501-510. As illustrated in this figure, a target parameter is selected for evaluation (501), which is an elastic modulus property in this illustration. Well data (e.g., wireline logging data) is obtained at a first depth interval for (502). The obtained formation data is used in determining a first parameter comprising at least one of photoelectric effect index, effective atomic number, and bulk density (503A), and a target parameter (the selected elastic modulus parameter) comprising a formation property that is different from the first parameter (503B), for a rock sample at the depth interval. Steps 502 and 503A-B can be repeated for at least one additional depth interval in the formation (504). The first parameter and the target parameter determined for the depth intervals in steps 502, 503A-B, and 504, is curve fitted to generate at least one of a mathematical function equation or cross-plot thereof relating the first and target parameters (505). A tomographic image is made of a rock sample obtained from a depth interval in the formation for generating a digital image of the rock sample (506). In step 507, at least one of photoelectric effect index, effective atomic number, or bulk density is determined in correspondence to the first parameter used in the curve-fitting in step 505 for the rock sample scanned in step 506, using the digital image generated for the rock sample in step 506. A high resolution target parameter of the rock sample scanned in step 506 is computed in step 508 comprising applying the mathematical function equation or cross-plot of step 505 to the corresponding parameter type of the photoelectric effect index, effective atomic number, and bulk density determined in step 507. In step 508, the high resolution target parameter can be calculated at higher resolution than for the original target parameter of step 503B where the same depth interval is compared. Steps 506, 507 and 508 can be repeated for samples obtained from at least one different depth interval of the formation, or for multiple samples obtained from the same depth interval, or both (509). The method indicated as process 500 in FIG. 5 can be used to compute a higher resolution value for a selected elastic modulus property as the target property at one or more depth intervals of a wellbore. As indicated by step 510, the process of steps 501-509 can be repeated for a different type of selected elastic modulus property as the target parameter, and then the entire process flow optionally again can be repeated for another different selected target property, one or more times. For example, steps 501-509 may be used to compute a high resolution target parameter value or values for compressional modulus (M) as the initially selected target parameter for evaluation, and then steps 501-509 may be repeated to compute a high resolution target parameter value or values for shear modulus (G) as a second selected target parameter for evaluation, and so forth. The formation data that was obtained in step 502 and the first parameter values determined in step 503 of a previous evaluation of a target parameter using process steps 502-509 may be applicable at least in part for use in a successive evaluation of a different target parameter. A method of the present invention can be based on a subset of these steps, and may include additional steps.

The preceding examples in FIGS. 4 and 5 show a target parameter defined as a function of a single parameter. As another example of the present invention, the target parameter can be defined as a function of multiple parameters. Referring to FIG. 6, a process flow 600 of a method of the present invention is illustrated which includes steps 601-610 which are similar in part to steps 401-410 of FIG. 4. As illustrated in this figure, the step 603A in the process flow 600 differs from step 403A used in the process flow 400 shown in FIG. 4 in that multiple parameters must be determined in this step (e.g., PEF or Zeff as one parameter, and RHOB as another), which are used in subsequent step 605 in of process flow 600 for providing a multivariable equation or plot that provides a mathematical relationship between the values determined for the selected target parameter (steps 603B-604), and the values determined for the multiple parameters (steps 603A-604). For example, if Vp is the selected target parameter in steps 601 and 603B (or a specific elastic modulus parameter such as E, G, M, etc.) and RHOB and PEF are the multiple parameters determined in step 603A, step 605 can be used to generate an equation for Vp as a function of RHOB and PEF. A curve fit of the target parameter values and multiple parameter values can expressed as a mathematical equation, a three-dimensional (3D) plot, or both. If plotted, the multivariable function can be plotted on a 3D graph, such as a cubic graph with x, y, and z axes, or other plotting techniques applicable to three or more variables. The multivariable equation or plot obtained in step 605 is used in step 608. A high resolution target parameter of the rock sample scanned in step 606 is computed in step 608 which comprises applying the multivariable mathematical function equation or cross-plot generated in step 605 to corresponding multiple types of parameters among the photoelectric effect index, effective atomic number, and bulk density determined in step 607. For example, in step 607, PEF or Zeff are shown as determined as one parameter, and RHOB as another, in correspondence to the types of multiple parameters determined in step 603A and used in step 605 in process flow 600. In step 608, the high resolution target parameter can be calculated at higher resolution than for the original target parameter of step 603B where the same depth interval is compared. As will be appreciated, the use of PEF or Zeff, and RHOB, as the multiple parameters used in the process flow 600 shown in FIG. 6 is for sake of illustration only. As shown in FIG. 6, various steps can be repeated for evaluating the selected target parameter, or the entire process can be repeated for a different selected target parameter.

In step 406 in FIG. 4, step 506 in FIG. 5, and step 606 in FIG. 6, with regard to the tomographic scan of the objects involved in the method of the present invention, the scan can be accomplished using a tomographical scanner, such as a multi-energy CT scanner (for instance, a dual energy X-ray CT scanner). Multiple energy X-ray imaging can be applied to a core or, where a core is not available, to drill cuttings, plugs or other types of samples. Tomographic digital images of the sample can be obtained from such multiple energy X-ray scanning of the sample. Parameter values for RHOB, PEF, or Zeff can be derived from the tomographic digital images. Multiple energy X-ray imaging technology which can be adapted for use in the methods of the present invention is described by Derzhi in U.S. Patent Application Publication No. 2013/0028371 A1, which is incorporated in its entirety by reference herein. A sample can be placed in a holding stage of the scanner device. Reference objects and calibration objects can be arranged within the scanner stage with the sample. The scanner itself can move to scan the target object (sample). In the alternative, the objects being scanned can move through a stationary scanner. Either option is possible. The types of materials, use, and arrangement of calibrations materials are further described, for example, in the incorporated U.S. Patent Application Publication No. 2013/0028371 A1. The CT scanner can be used at a nominal resolution, for example, of from about 10 μm to about 50 μm, or from about 10 μm to about 45 μm, or from about 10 μm to about 25 μm, or from about from about 10 μm to about 15 μm, or other values. There is no specific theoretical limit on the lower limit size of the resolution. As indicated, the samples can be scanned with X-rays using dual energies or more than two energies.

In step 407 in FIG. 4, step 507 in FIG. 5, and step 607 in FIG. 6, the multiple energy X-ray imaging technology can be used to provide bulk density and photoelectric effect (PEF) (or effective atomic number, Zeff) inputs for use in methods of the present application. Multiple energy X-ray imaging can provide two outputs which are the bulk density and the photoelectric effect index (or effective atomic number). The photoelectric effect index can be mostly driven by the mineralogy, and can be converted to effective atomic number (Zeff), or vice versa, by the indicated equation (2). Incorporated U.S. Patent Application Publication No. 2013/0028371 A1 describes methods which can be used herein for reconstructing the data set obtained from the scanner to calculate RhoB and $Z_{eff}$ (or PEF) from multiple energy, e.g., high and low energy, CT values. For example, a scan of the sample can be run, a 3D image is obtained with CT value for each voxel, similar to the method indicated in the incorporated U.S. Patent Application Publication No. 2013/0028371, and then all the voxels associated with each sample can be taken and an average is calculated on them. Thus, each sample can have an average value. This is performed for each different energy scan (e.g., high and low energy scans). So if a dual energy scan is performed, each sample has an averaged high and low CT value. These two values for each sample and each of the reference objects can be used to process and compute the bulk density and effective atomic number.

A method for estimating the bulk density and/or effective atomic number of a target object can involve, for example, one or more of the following steps which can be performed once or multiple times:

i. performing a scan of two or more reference objects and three or more calibration objects,
ii. obtaining a functional relationship between bulk density error and effective atomic number using scan values from the reference objects and the calibration objects,
iii. performing a scan of the target object and the three or more calibration objects,
iv. obtaining uncorrected density and effective atomic number for the target object,
v. obtaining bulk density corrections using the functional relationship between bulk density error and effective atomic number from the reference objects, and the effective atomic number for the target object, and
vi. obtaining the corrected bulk density using the bulk density corrections. Additional details on this methodology are included in the indicated incorporated patent application publication herein.

As indicated, PEF can be calculated from the effective atomic number using equation (2).

The present invention further relates to a system for implementing one or more of the methods as described above. Referring to FIG. 7, a system 700 is shown which can be adapted for performing the present methods. As shown in this example, a well logging system 701 (e.g., a wireline logging system) is used to obtain well data 702, such as the kinds indicated herein. The well data 702 of the well logging system 701 can be transferred to a computer or computers 706 having program instructions for carrying out the curve fitting of the well data to generate a formulaic relationship between different parameters at one or more different depth intervals of the formation. Core samples or other well samples are collected from one or more depth intervals of the formation and prepared at a station or stations 703 for tomographical scanning. The samples are scanned using a multi-energy CT scanner 704. The system can comprise one or more computer systems for processing images and computing rock properties according to methods of the present invention. For example, the 3D image output 705 of the scanner for a sample can be transferred to the computer or computers 706 having program instructions for carrying out the 3D image analysis, and the indicated data and computational analysis to determine a photoelectric effect index and/or effective atomic number for a scanned sample to which the formulaic relationship can be applied to estimate one or more formation properties of the scanned sample. Records of inputted data and output/results generated by the computer(s) 706 for these computations can be transmitted to one or more devices 707, such as a display, a printer, data storage medium, or combinations of these. The computer programs used for the analyses and computations can be stored, as a program product, on at least one computer usable storage medium (e.g. a hard disk, a flash memory device, a compact disc, a magnetic tape/disk, or other media) associated with at least one processor (e.g., a CPU) which is adapted to run the programs, or may be stored on an external computer usable storage medium (not shown) which is accessible to the computer processor.

The CT scanning, computing and/or output/storage systems used in the systems of the present invention can be located and used off-site or on-site with respect to where the samples and well data are obtained. If used off-site, samples can be transported to the location where the system is located. If used on-site, the CT scanning, computing and/or output/storage systems used in the systems of the present invention optionally can be used in a mobile enclosure such as a trailer, van, motor coach or similar device, such that it can be transported to a well site and analyses run on-site.

The present invention also includes the following aspects/embodiments/features in any order and/or in any combination:

1. A method for evaluating a geological formation, comprising:
(a) determining a first parameter comprising photoelectric effect index, effective atomic number, or bulk density, and a target parameter comprising a formation property that is different from the first parameter, for a rock sample at a depth interval in a formation, using formation data;
(b) repeating (a) for at least one additional depth interval in the formation;
(c) curve-fitting the first parameter and the target parameter determined for the depth intervals of (a)-(b) to generate at least one of a mathematical function equation or cross-plot thereof relating the first and target parameters;
(d) generating a tomographic image of a rock sample obtained from a depth interval in the formation for generating a digital image of the rock sample;
(e) determining photoelectric effect index, effective atomic number, or bulk density in correspondence to the first parameter used in the curve-fitting in (c) for the rock sample of (d), using the digital image generated for the rock sample in (d); and
(f) computing a high resolution target parameter for the rock sample of (d) comprising applying the mathematical function equation or cross-plot of (c) to the photoelectric effect index, effective atomic number, or bulk density determined in (e).

2. The method of any preceding or following embodiment/feature/aspect, wherein the formation data comprises well data, laboratory data, and non-tomographic based theoretical modeling data.

3. The method of any preceding or following embodiment/feature/aspect, wherein the depth intervals of (a)-(b) are from about 1 foot to about 1.5 feet (about 30 cm to about 46 cm).

4. The method of any preceding or following embodiment/feature/aspect, wherein the depth interval of (d) is from about 1 mm to about 10 cm.

5. The method of any preceding or following embodiment/feature/aspect, wherein the formation property is an elastic property.

6. The method of any preceding or following embodiment/feature/aspect, wherein the formation property is gamma ray, electrical resistivity, porosity, compressional modulus, shear modulus, Poisson's ratio, Young's modulus, compressional-wave velocity (Vp), or shear-wave velocity (Vs).

7. The method of any preceding or following embodiment/feature/aspect, wherein the curve-fitting comprises a least squares fit.

8. The method of any preceding or following embodiment/feature/aspect, further comprising repeating step (b) at least once.

9. The method of any preceding or following embodiment/feature/aspect, further comprising (h) repeating steps (e), (f) and (g) for at least one additional depth interval.

10. The method of any preceding or following embodiment/feature/aspect, wherein (d) comprises performing an X-ray CT scan of the rock sample obtained from a depth interval in the formation for generating the digital image of the rock sample, and (e) comprises determining at least one of photoelectric effect index, effective atomic number, or bulk density in correspondence to the first parameter used in the curve-fitting in (c) for the rock sample of (d), using CT values obtained for voxels in the digital image generated for the rock sample from the X-ray CT scan in (d).

11. The method of any preceding or following embodiment/feature/aspect, wherein the X-ray CT scan is a multi-energy X-ray CT scan.

12. The method of any preceding or following embodiment/feature/aspect, wherein the formation comprises a lithological lamination thicknesses of less than about 10 cm.

13. The method of any preceding or following embodiment/feature/aspect, wherein the formation comprises shale.

14. The method of any preceding or following embodiment/feature/aspect, wherein the formation comprises horizontally laminated shale.

15. The method of any preceding or following embodiment/feature/aspect, wherein the first parameter is photoelectric effect index or effective atomic number, and the target parameter is an elastic modulus.

16. The method of any preceding or following embodiment/feature/aspect, wherein the first parameter is one of photoelectric effect index and effective atomic number.

17. The method of any preceding or following embodiment/feature/aspect, further comprising (g) directing drilling of a wellbore in the formation based at least in part on the computed at least one formation property of the rock sample in (f).

18. The present invention also relates to a method for evaluating a geological formation, comprising:
(a) determining a first parameter comprising photoelectric effect index, effective atomic number, or bulk density, and a target parameter comprising an elastic modulus property, for a rock sample at a depth interval in a formation, using well logging data;
(b) repeating (a) for at least one additional depth interval in the formation;
(c) curve-fitting the first parameter and the target parameter determined for the depth intervals of (a)-(b) to generate at least one of a mathematical function equation or cross-plot thereof relating the first and target parameters;
(d) performing an X-ray CT scan of a rock sample obtained from a depth interval in the formation for generating a digital image of the rock sample;
(e) determining photoelectric effect index, effective atomic number, or bulk density in correspondence to the first parameter used in the curve-fitting in (c) for the rock sample of (d), using CT values obtained for voxels in the digital image generated for the rock sample from the X-ray CT scan in (d); and
(f) computing a high resolution target parameter for the rock sample of (d) comprising applying the mathematical function equation or cross-plot of (c) to the photoelectric effect index, effective atomic number, or bulk density determined in (e).

19. The method of any preceding or following embodiment/feature/aspect, further comprising repeating steps (d), (e), and (f) at least one time for a rock sample obtained from a different depth interval of the formation.

20. The method of any preceding or following embodiment/feature/aspect, wherein the elastic modulus property comprises one of shear modulus and compressional modulus.

21. The method of any preceding or following embodiment/feature/aspect, further comprising (g) directing drilling of a wellbore in the formation based at least in part on the computed at least one formation property of the rock sample in (f).

22. The present invention also relates to a method for evaluating a geological formation, comprising:

(a) determining multiple parameters among photoelectric effect index, effective atomic number, and bulk density, and a target parameter comprising a formation property that is different from the multiple parameters, for a rock sample at a depth interval in a formation using formation data (e.g., well data, laboratory data, non-tomographic theoretical modeling data, or any combinations thereof);
(b) repeating (a) for at least one additional depth interval in the formation;
(c) curve-fitting the multiple parameters and the target parameter determined for the depth intervals of (a)-(b) to generate at least one of a multivariable mathematical function equation or 3D plot thereof relating the target parameter as a function of the multiple parameters;
(d) generating a tomographic image of a rock sample obtained from a depth interval in the formation for generating a digital image of the rock sample;
(e) determining more than one of photoelectric effect index, effective atomic number, or bulk density in correspondence to the multiple parameters used in the curve-fitting in (c) for the rock sample of (d), using the digital image generated for the rock sample in (d); and
(f) computing a high resolution target parameter for the rock sample of (d) comprising applying the multivariable mathematical function equation or 3D plot of (c) to the more than one of photoelectric effect index, effective atomic number, or bulk density determined in (e).

23. The present invention also relates to a system for evaluating a geological formation, comprising:
(a) one or more computer systems operable for storing and processing inputted data comprising a first parameter comprising photoelectric effect index, effective atomic number, or bulk density, and a target parameter different from the first parameter, determined for a rock sample at each of multiple depth intervals in a formation wherein the inputted data comprises at least one of well data, laboratory data, and non-digital image based theoretical modeling data;
(b) one or more computer systems operable to curve-fit the first parameter and the target parameter determined for the multiple depth intervals to generate at least one of a mathematical function equation or cross-plot thereof relating the first and target parameters;
(c) an X-ray scanner operable to scan a rock sample from the formation to generate a digital image of the rock sample;
(d) one or more computer systems for computing photoelectric effect index, effective atomic number, or bulk density in correspondence to the first parameter used in the curve-fitting in (b) for the rock sample of (c) using CT values obtained for voxels in the rock sample from the X-ray CT scan;
(e) computing a high resolution target parameter for the rock sample of (c) comprising applying the mathematical function equation or cross-plot of (b) to photoelectric effect index, effective atomic number, or bulk density determined in (d);
(f) at least one device to display, print, or store results of the computations.

24. The system of any preceding or following embodiment/feature/aspect, wherein the X-ray scanner is a multi-energy CT scanner operable to scan a rock sample from the formation to generate a digital image of the rock sample.

25. The system of any preceding or following embodiment/feature/aspect, further comprising a well logging system capable of producing well data that is inputtable to the one or more computer systems.

26. The present invention also relates to a computer program product on a non-transitory computer usable storage medium that, when performed on a processor in a computerized device provides a method for performing computations of one or more or all of the indicated steps of the preceding methods and systems.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount or other value or parameter is given as either a range, preferred range, or list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range. Other embodiments of the present invention will be apparent to those skilled in the art form consideration of the present specification and practice of the present invention disclosed herein. It is intended that the present specification and examples be considered as exemplary only with a true scope and spirit of the invention being indicated by the following claims and equivalents thereof

What is claimed is:

1. A method for evaluating a geological formation, comprising:
    (a) determining a first parameter comprising photoelectric effect index, effective atomic number, or bulk density, and a target parameter comprising a formation property that is different from the first parameter, for a rock sample at a depth interval in a formation, using formation data;
    (b) repeating (a) for at least one additional depth interval in the formation;
    (c) curve-fitting the first parameter and the second parameter determined for the depth intervals of (a)-(b) to generate at least one of a mathematical function equation or cross-plot thereof relating the first and target parameters;
    (d) generating a tomographic image of a rock sample obtained from a depth interval in the formation for generating a digital image of the rock sample;
    (e) determining photoelectric effect index, effective atomic number, or bulk density in correspondence to the first parameter used in the curve-fitting in (c) for the rock sample of (d), using the digital image generated for the rock sample in (d); and
    (f) computing a high resolution target parameter for the rock sample of (d) comprising applying the mathematical function equation or cross-plot of (c) to the photoelectric effect index, effective atomic number, or bulk density determined in (e).

2. The method of claim 1, wherein the well data comprises at least one of well data, laboratory data, and non-tomographic based theoretical modeling data.

3. The method of claim 1, wherein the depth intervals of (a)-(b) are from about 1 foot to about 1.5 feet (about 30 cm to about 46 cm).

4. The method of claim 1, wherein the depth interval of (d) is from about 1 mm to about 10 cm.

5. The method of claim 1, wherein the formation property is an elastic property.

6. The method of claim 1, wherein the formation property is gamma ray, electrical resistivity, porosity, compressional modulus, shear modulus, Poisson's ratio, Young's modulus, compressional-wave velocity (Vp), or shear-wave velocity (Vs).

7. The method of claim 1, wherein the curve-fitting comprises a least squares fit.

8. The method of claim 1, further comprising repeating step (b) at least once.

9. The method of claim 1, further comprising (h) repeating steps (e), (f) and (g) for at least one additional depth interval.

10. The method of claim 1, wherein (d) comprises performing an X-ray CT scan of the rock sample obtained from a depth interval in the formation for generating the digital image of the rock sample, and (e) comprises determining at least one of photoelectric effect index, effective atomic number, or bulk density in correspondence to the first parameter used in the curve-fitting in (c) for the rock sample of (d), using CT values obtained for voxels in the digital image generated for the rock sample from the X-ray CT scan in d).

11. The method of claim 1, wherein the X-ray CT scan is a multi-energy X-ray CT scan.

12. The method of claim 1, wherein the formation comprises a lithological lamination thicknesses of less than about 10 cm.

13. The method of claim 1, wherein the formation comprises shale.

14. The method of claim 1, wherein the formation comprises horizontally laminated shale.

15. The method of claim 1, wherein the first parameter is photoelectric effect index or effective atomic number, and the target parameter is an elastic modulus.

16. The method of claim 1, wherein the first parameter is one of photoelectric effect index and effective atomic number.

17. The method of claim 1, further comprising (g) directing drilling of a wellbore in the formation based at least in part on the computed at least one formation property of the rock sample in (f).

18. A method for evaluating a geological formation, comprising:
(a) determining a first parameter comprising photoelectric effect index, effective atomic number, or bulk density, and a target parameter comprising an elastic modulus property, for a rock sample at a depth interval in a formation, using well logging data;
(b) repeating (a) for at least one additional depth interval in the formation;
(c) curve-fitting the first parameter and the second parameter determined for the depth intervals of (a)-(b) to generate at least one of a mathematical function equation or cross-plot thereof relating the first and target parameters;
(d) performing an X-ray CT scan of a rock sample obtained from a depth interval in the formation for generating a digital image of the rock sample;
(e) determining photoelectric effect index, effective atomic number, or bulk density in correspondence to the first parameter used in the curve-fitting in (c) for the rock sample of (d), using CT values obtained for voxels in the digital image generated for the rock sample from the X-ray CT scan in (d); and
(f) computing a high resolution target parameter for the rock sample of (d) comprising applying the mathematical function equation or cross-plot of (c) to the photoelectric effect index, effective atomic number, or bulk density determined in (e).

19. The method of claim 18, further comprising repeating steps (d), (e), and (f) at least one time for a rock sample obtained from a different depth interval of the formation.

20. The method of claim 18, wherein the elastic modulus property comprises one of shear modulus and compressional modulus.

21. The method of claim 18, further comprising (g) directing drilling of a wellbore in the formation based at least in part on the computed at least one formation property of the rock sample in (f).

22. A method for evaluating a geological formation, comprising:
(a) determining multiple parameters among photoelectric effect index, effective atomic number, and bulk density, and a target parameter comprising a formation property that is different from the multiple parameters, for a rock sample at a depth interval in a formation using formation data;
(b) repeating (a) for at least one additional depth interval in the formation;
(c) curve-fitting the multiple parameters and the target parameter determined for the depth intervals of (a)-(b) to generate at least one of a multivariable mathematical function equation or 3D plot thereof relating the target parameter as a function of the multiple parameters;
(d) generating a tomographic image of a rock sample obtained from a depth interval in the formation for generating a digital image of the rock sample;
(e) determining more than one of photoelectric effect index, effective atomic number, or bulk density in correspondence to the multiple parameters used in the curve-fitting in (c) for the rock sample of (d), using the digital image generated for the rock sample in (d); and
(f) computing a high resolution target parameter for the rock sample of (d) comprising applying the multivariable mathematical function equation or 3D plot of (c) to the more than one of photoelectric effect index, effective atomic number, or bulk density determined in (e).

23. A system for evaluating a geological formation, comprising:
(a) one or more computer systems operable for storing and processing inputted data comprising a first parameter comprising photoelectric effect index, effective atomic number, or bulk density, and a target parameter different from the first parameter, determined for a rock sample at each of multiple depth intervals in a formation wherein the inputted data comprises at least one of well logging data, laboratory data, and non-digital image based theoretical modeling data;
(b) one or more computer systems operable to curve-fit the first parameter and the target parameter determined for the multiple depth intervals to generate at least one of a mathematical function equation or cross-plot thereof relating the first and target parameters;
(c) an X-ray scanner operable to scan a rock sample from the formation to generate a digital image of the rock sample;
(d) one or more computer systems for computing photoelectric effect index, effective atomic number, or bulk density in correspondence to the first parameter used in the curve-fitting in (b) for the rock sample of (c) using CT values obtained for voxels in the rock sample from the X-ray CT scan;

(e) computing a high resolution target parameter for the rock sample of (c) comprising applying the mathematical function equation or cross-plot of (b) to the photoelectric effect index, effective atomic number, or bulk density determined in (d);
(f) at least one device to display, print, or store results of the computations.

24. The system of claim 23, wherein the X-ray scanner is a multi-energy CT scanner operable to scan a rock sample from the formation to generate a digital image of the rock sample.

25. The system of claim 23, further comprising a well logging system capable of producing well data that is inputtable to the one or more computer systems.

26. A computer program product on a non-transitory computer usable storage medium that, when performed on a processor in a computerized device provides a method for performing computations of one or more or all of the indicated steps of the method of claim 1.

\* \* \* \* \*